(12) United States Patent
Moore et al.

(10) Patent No.: US 6,727,073 B1
(45) Date of Patent: Apr. 27, 2004

(54) METHOD FOR DETECTING ENTERIC DISEASE

(75) Inventors: Norman Moore, North Berwick, ME (US); Phillip I. Tarr, Seattle, WA (US)

(73) Assignee: Binax, Inc., Portland, ME (US)

( * ) Notice: Subject to any disclaimer, the term of this patent is extended or adjusted under 35 U.S.C. 154(b) by 0 days.

(21) Appl. No.: 09/443,211

(22) Filed: Nov. 19, 1999

(51) Int. Cl.$^7$ ................................................ G01N 33/53

(52) U.S. Cl. ..................... 435/7.32; 435/7.37; 435/7.94; 435/28.7; 435/287.8; 435/30; 436/518; 436/526; 436/536; 436/538; 436/161; 436/810

(58) Field of Search ................... 435/5, 7.37, 7.94, 435/30, 287.7, 287.8, 7.32; 436/518, 526, 536, 538, 161, 810

(56) References Cited

U.S. PATENT DOCUMENTS

| | | | |
|---|---|---|---|
| 5,089,391 | A | 2/1992 | Buechler et al. |
| 5,124,252 | A | 6/1992 | Guerrant et al. |
| 5,126,276 | A | 6/1992 | Fish et al. |
| 5,158,869 | A | 10/1992 | Pouletty et al. |
| 5,602,040 | A | 2/1997 | May et al. |
| 5,622,871 | A | 4/1997 | May et al. |
| 5,707,818 | A | 1/1998 | Chudzik et al. |
| 5,714,389 | A | 2/1998 | Charlton et al. |
| 5,795,725 | A | 8/1998 | Buechler et al. |
| 5,807,752 | A | * 9/1998 | Brizgys et al. |
| 5,846,838 | A | 12/1998 | Chandler |
| 5,869,345 | A | 2/1999 | Chandler |
| 5,877,028 | A | 3/1999 | Chandler et al. |
| 5,910,421 | A | 6/1999 | Small et al. |
| 6,136,549 | A | * 10/2000 | Feistel |

OTHER PUBLICATIONS

Hasan et al., Journal of Clinical Mircobiology. Jan. 1994. vol. 32, No. 1, pp. 249–252.*
Quix ™ Rapid *E. coli* 0157 Strip Test. 1997.*
Re et al., Methods in Immunodiagnosis. Edited by Rose et al. 1980, pp. 147–158.*
Tijssen, *Practice and Theory of Enzyme Immunoassays*, 1985, pp. 105–115, Elsevier, USA.
Hughes et al., "Preparation of Colloidal Gold Probes", *Methods in Molecular Biology*, vol. 80, Humana Press, USA.

(List continued on next page.)

*Primary Examiner*—Bao-Thuy L. Nguyen
(74) *Attorney, Agent, or Firm*—Mary Helen Sears

(57) ABSTRACT

A method for determining and diagnosing inflammatory enteric disease using an immunochromatographic test device having a multiplicity of test zones. The method tests for the presence of at least one enteric pathogen and at least one of certain inflammatory enteric disease markers. The enteric pathogens tested for can be any number of enteric pathogens such as the pathogens *E. coli* O157, Campylobacter, Salmonella, Listeria, Shigella, and Yersinia. The inflammatory enteric disease markers tested for are fecal lactoferrin, a bacteria marker, a virus marker, and a protozoa marker. Positive results for any one of the pathogens indicates that pathogen as the cause of the inflammatory enteric disease. Positive results for fecal lactoferrin indicate an inflammatory condition of the intestines. Positive results for the bacteria, virus, protozoa markers indicate respectively a bacterial, viral, or protozoan cause of infection as the cause of the disease. Liquid fecal sample is mixed with a mixture containing antibodies to the pathogens and the markers. These antibodies are conjugated to a label. Each test zone on the test device has immovably fixed upon it a complementary antibody that binds specifically with one of the labeled antibodies in the mixture. Positive results appear as a stripe across the corresponding test zone.

7 Claims, 2 Drawing Sheets

OTHER PUBLICATIONS

Jennes et al., "Synthesis and Use of Colloidal Gold–Coupled Receptor Ligands", *Methods in Enzymology*, vol. 124, Academic Press, 1986, USA.

Boerlin et al., "Assoications between Virulence FActors of Shiga Toxin–Producing *Escherichia coli* and Disease in Humans", *J. of Clinical Microbiology*, Mar. 1999, pp. 497–503, USA.

Bokete et al., "Genetic and Phenotypic Analysis of *Escheria coli* with Enteropathogenic Charatcteristics Isolated from Seattle Children", *J. of Infectious Diseases*, 1997, vol. 175, pp. 1382–1389, USA.

Schmidt et al.,"Non–O157:H7 Pathogenic Shiga Toxin–Producing *Escheria coli*: Phenotypic and Genetic Profiling of Virulence Traits and Evidence for Clonality", *J. of Infectious Deseases*, vol. 179, pp. 115–123, 1999, USA.

Huicho et al., "Fecal lactoferrin, fecal leukocytes and occult blood in the diagnostic approach to childhood invasive diarrhea", *Pediatric Infectious Disease J.*, V. 16, pp. 644–647, 1997, USA.

Huicho et al., "Fecal screening tests in the approach to acute infectious diarrhea: a scientific review", *Pediatric Infectious Disease J.*, V. 15, pp. 486–494, 1996, USA.

Uchida et al., "Immunochemical Detection of Human Lactoferrin in Feces as a New Marker for Inflammatory Gastrointestinal Disorders and Colon Cancer", *Clinical Biochemistry*, vol. 27, pp. 259–264, 1994, USA.

Gabriel et al., "Accuracy of fecal lactoferrin and other stool tests for diagnosis of invasive diarrhea at a Colombian pediatric hospital", *Pediatric Infectious Disease J.*, V. 18, pp. 342–346, 1999, USA.

Sugi et al., "Fecal Lactoferrin as a Marker for Disease Activity in Inflammatory Bowel Disease: Comparison with Other Neutrophil–derived Proteins", *The American J. of Gastroenterology*, vol. 91, pp. 927–934, 1996, USA.

Choi et al., "To Culture or Not To Culture: Fecal Lactoferrin Screening for Inflammatory Bacterial Diarrhea", *J. of Clinical Microbiology*, vol. 34, pp. 928–932, 1996, USA.

Scerpella et al., "Evaluation of a New Latex Agglutination Test for Fecal Lactoferrin in Travelers' Diarrhea", *J. of Travel Medicine* vol. 1, pp. 68–71, 1994, USA.

Fine, et al., "Utility of a Rapid Fecal Latex Agglutination Test Detecting the Neutrophil Protein, Lactoferrin, for Diagnosing Inflammatory Causesd of Chronic Diarrhea", *American J. of Gastroenterology*, vol. 93, No. 8, 1998, pp. 1300–1305. USA.

* cited by examiner

METHOD FOR DETECTING ENTERIC DISEASE

BACKGROUND OF THE INVENTION

1. Field of the Invention

The present invention relates to the field of immunochromatographic assays. More particularly, the present invention relates to a method for detecting enteric pathogens in fecal specimens. More particularly yet, the present invention relates to a method for detecting the presence of one or more specific enteric pathogens from the simultaneous assay for several enteric pathogens. Most particularly, the present invention relates to a method for detecting the presence or absence of several enteric pathogens and concurrently applying one or more general tests for an inflammatory condition of the intestines.

2. Description of Prior Art

Enteric pathogens can cause severe illness in people and affect a large number of people within a short period of time. The U.S. Centers for Disease Control estimates that there are five million cases of foodborne illnesses per year in the United States with up to 5,000 deaths. *Campylobacter jejuni* and Salmonella are the leading causes of foodborne illnesses; *E. coli* O157 is less frequent, but is significant in disease control because this strain of *E. coli*, the most noted of the enterohemorrhagic *E. coli* bacteria, causes the majority of severe disease from *E. coli* and is also a cause of large epidemics. Other strains of *E. coli*, such as O111, have also been implicated in foodborne outbreaks. Although the number of illnesses from *E. coli* O157 is low relative to the numbers of cases of *Campylobacter jejuni* or Salmonella, this *E. coli* pathogen is significant because the rate of mortality is much higher and the treatment significantly different. Some antibiotics can have a detrimental effect on patient health if the patient is suffering from an illness caused by an enterohemorrhagic *E. coli* that has not been diagnosed. For this reason, before prescribing antibiotics for a patient apparently suffering from an illness caused by a pathogen, it is important to determine whether *E. coli* bacteria is the cause in order to avoid prescribing medication detrimental to the health of the patient. Rapid determination of the cause of the illness is thus a critical factor in providing the timely and proper care of the ill. Moreover, it is critical to determine the possible sources of contamination as quickly as possible in order to take appropriate steps to eliminate them.

A method to rapidly screen patients for enteric illnesses would greatly increase the ability of medical personnel to accurately diagnose the cause of the illness and provide appropriate treatment, thus accelerating the rate of patient recovery. Furthermore, a method for rapid screening for enteric pathogens also has great economic value because it can focus valuable resources. For example, rapid screening can be used to rule out certain pathogens as a cause of illness before making the decision to use the more costly methods of culturing a specimen for a pathogen that cannot be readily detected by a rapid screening device. Use of a method for rapidly screening patients for enteric illnesses that can be performed reliably by unskilled persons is also a more cost-effective use of personnel resources than the use of a method that requires the attention of skilled personnel.

Enteric pathogens are not the only cause of diarrhea. Other causes include food sensitivities, allergic reactions, side effects from medication, and psychosomatic factors. The treatment for diarrhea resulting from such non-pathogenic factors is very different than the anti-microbial treatment of pathogenic diarrhea. A screening method that would give an indication of whether the cause of the diarrhea is infectious or non-infectious, inflammatory or non-inflammatory would provide valuable diagnostic information to a treating physician. A common response to enteric pathogens is an inflammation of the intestines. In contrast, an inflammatory condition of the intestines is generally lacking when the cause of the diarrhea is non-infectious or non-immune. Thus, it is very useful to assay for a marker that is associated with intestinal inflammation and that is absent or present only in very low concentrations in the absence of such inflammation. The detection of such a general marker is useful, for example, in a situation in which none of the specific pathogens assayed for appears to be present. The knowledge that the "inflammation" marker is present then will lead to a continued search for the pathogen causing the inflammation, and will also provide additional causes for symptoms such as inflammatory bowel disease. Thus, a method that not only tests for multiple enteric pathogens simultaneously, but also tests for an inflammatory condition of the intestines would provide the physician with additional valuable diagnostic information. Furthermore, a method that would also test for a bacterial, viral, or protozoan cause of enteric disease would provide further valuable diagnostic information in the situation where none of the specific pathogens being assayed for appears to be present.

The immunoassay technique, which relies on the specific binding action between an antigen or a hapten and a corresponding antibody, has proven to be a reliable method for determining the presence (or absence) of a pathogen in a specimen. A class of devices known as immunochromatographic test (ICT) devices uses the immunoassay technique in combination with a label that is conjugated with the antibody and is now commonly used for rapid, reliable field tests to determine the presence or absence of a particular analyte. The label, when attached to antibody/antigen molecules that are then amassed together in a specific, restricted area, becomes readily detectable by the naked human eye, or by a scanning device, depending on the type of label used. In general, the label can be a particle of latex, gold, or carbon, a radioactive particle, a magnetic particle, or have other physical or chemical properties that allow it to be fixed or attracted to a certain defined area. ICT devices that use the sandwich technique are particularly easy to use. With this technique, labeled antibody that binds with the specific antigen to be assayed is mixed with the sample that is suspected of containing the specific antigen. If the antigen is present in the sample, the labeled antibody binds with the antigen to form a label-antibody-antigen complex. A second antibody that is immovably fixed at a test zone and that also binds with the specific antigen binds the label-antibody-antigen complex at the test zone. A positive result is made visible by the accumulation of the label at the test zone. Such devices are economical and can be used by unskilled workers. Thus, a method that uses such an ICT device to determine, in a single assay, the presence or absence of multiple enteric pathogens, in particular, multiple enteric pathogens, plus a general marker for an inflammatory condition of the intestines would provide valuable diagnostic information to a treating physician.

Several types of such ICT devices are known. Most are the "dipstick" type in which a test strip is encased in a hollow housing with a bibulous pad extending from one end. This pad is dipped into the liquid sample and draws the liquid by capillary ("wicking") action up onto a section of the test strip that contains a labeled antibody, i.e., a label conjugated to an antibody that will specifically bind with the antigen being assayed. The labeled antibody moves with the liquid that is being drawn by the capillary action further along the test strip and, if the specific antigen to which the antibody binds is present in the liquid sample, the labeled antibody will bind with the antigen, forming a labeled antibody-antigen complex. This complex continues to flow with the liquid along the test strip. Downstream from the area containing the conjugated antibody is a test zone. This test zone is typically a nitrocellulose pad into which a second binding partner, an antibody that binds to the same antigen as the labeled antibody, but to a second epitope of the antigen, has been immovably fixed. The fixed antibody will attach to the labeled antibody-antigen complex that flows onto the test zone and will bind the complex to the test zone. The presence of an antigen being assayed is then visible as a stripe across the test zone or otherwise readily detectable. The excess liquid continues to flow past the test zone across a control zone. There are a number of well-known means in the field of immunoassay of creating a control zone, such as embedding into the control zone a binding partner that binds non-specifically to one or more of the labeled antibodies contained on the conjugate section, or to a labeled analyte added to the liquid sample for the purpose of binding with the non-specific binding partner at the control zone. A properly completed test will always show a visible stripe across the control zone or, if a radioisotope or magnetic particle is used as a label, an otherwise readily detectable stripe. Typically, for those devices using a colored label, the housing of the ICT device has a window through which to view the test zone and the control zone. Devices of this type have been disclosed in May et al. (U.S. Pat. No. 5,622,871; issued Apr. 22, 1997) and Charlton et al. (U.S. Pat. No. 5,714,389; issued Feb. 3, 1998).

Chandler (U.S. Pat. No. 5,869,345; issued 1999, and U.S. Pat. No. 5,877,028; issued 1999) discloses an ICT device that is a two-panel card containing a test strip on one panel and a sample well on the other panel. These patents, which are assigned to SmithKline Diagnostics, Inc. but licensed exclusively to the Assignee of the present invention, are incorporated herein by reference. The Chandler devices also uses the sandwich technique described above with the dipstick devices, but have a particular advantage in that they allow the sample to be prepared for the test directly on the test card, rather than in a separate vessel. When the test card is closed, liquid from the sample well flows onto the test strip. As with the other devices, a window is provided through which to view the results.

Chandler discloses methods for detecting an analyte using the ICT card disclosed in the patents cited above. Similarly, Charlton et al. and May et al. disclose methods for detecting an analyte using the device disclosed in the respective patent. Guerrant et al. (U.S. Pat. No. 5,124,252; issued 1992) discloses a method for distinguishing inflammatory diarrhea from non-inflammatory diarrhea, using radial immunodiffusion assay, latex agglutination assay, or enzyme-linked immunosorbent assay. None of these methods discloses a method for rapid, inexpensive screening for enteric disease that is desirable in diagnosing and treating inflammatory intestinal illness caused by specific enteric pathogens.

What is needed, therefore, is a method that will test for multiple enteric pathogens simultaneously using an ICT device. What is further needed is such a method that will test simultaneously for multiple enteric foodborne pathogens. What is yet further needed is such a method that will indicate an inflammatory condition of the intestines. What is still further needed is such a method that will indicate a bacterial, viral, or protozoan cause of enteric disease. Finally, what is needed is such a method that will provide rapid screening ability, is economical, and can be reliably used by unskilled persons.

SUMMARY OF THE INVENTION

It is an object of the present invention to provide a method that will test simultaneously for multiple enteric pathogens. It is a further object of the present invention to provide such a method that will test for multiple enteric foodborne pathogens. It is a yet further object to provide such a method that will test for an inflammatory condition of the intestines. It is a still further object to provide such a method that will test for a bacterial, viral, or protozoan cause of enteric disease.

Finally it is an object of the present invention to provide such a method that will provide highly accurate results within a few minutes, is economical, and can be reliably used by unskilled persons.

The present invention is a method for testing a fecal sample for the presence of one or more enteric pathogens, such a E. coli O157, Campylobacter jejuni, Salmonella, Listeria, Shigella, and Yersinia, Cryptosporidium, Giardia, or a subcombination thereof. These pathogens are common causes of enteric illness or are significant because of a high rate of mortality. It should be understood, however, that the method of the present invention can be used to screen for any number of enteric pathogens including such enteric pathogens as E. coli O26, E. coli O103, E. coli O111, E. coli O121, and E. coli O145. The method of the present invention also tests for the presence of fecal lactoferrin as an indicator of inflammation, and for a bacterial, viral, or protozoan cause of inflammation. The method tests for antigens of the enteric pathogens and the lactoferrin, and for bacterial, viral, or protozoan cause of inflammation, on a single test strip of an ICT device. The method uses the sandwich technique of binding a labeled antibody to a specific antigen and fixing the labeled antigen at a test zone by means of an immovably fixed second antibody that also binds to the specific antigen. The terms "antigen" and "antibody" are used herein in the singular form to refer to a plurality of exemplars of the same particular antigen or antibody, respectively.

According to the method of the present invention, liquid from a fecal sample is applied to an immunochromatographic test device having a detection area and a carrier bearing multiple specific labeled antibodies for the multiple antigens being assayed for, each specific antibody binding to one specific antigen of the multiple antigens. As mentioned above, numerous types of such devices are known. Generally, the labeled antibodies are mixed with the liquid from the sample and this mixture then flows onto the detection area. In some devices, the liquid from the sample may first flow onto the detection area and the labeled antibodies then be admixed onto the detection area. The description that follows is based on a unidirectional flow device in which the flow of liquid to be tested is such that the labeled antibodies are mixed with the liquid and the mixture then flows onto the detection area and then onto the control area. It should be understood, however, that the sequence in which the labeled antibodies are mixed with the liquid from the sample is not critical to the immunochromatographic test, as long as the device provides for a mixture at the detection area of labeled antibodies and the liquid to be tested. Thus, bidirectional flow devices, such as are disclosed in Chandler, supra, can also be used to perform the test according to the method of the present invention.

The labeled antibodies are conjugated to a label, such as a gold, colored latex, or carbon particle, an enzyme, a magnetic particle, a radioisotope, or other type of label that will allow a chromatographic indication of a positive or negative result. The liquid from the sample will cause these labeled antibodies to be released from the carrier and they will then flow with the liquid. If an antigen being assayed for is present in the liquid, the specific antibody will attach to it, forming a label-antibody-antigen complex with the label attached to the antibody serving as a visual label for the antigen. The liquid then flows onto a detection area such as a nitrocellulose pad or other carrier that contains multiple test zones and a control zone. Each test zone is separate and distinct from every other test zone and carries a second specific antibody for one of the antigens being assayed. This second antibody attaches to the same antigen that the labeled antibody attached to, but to a second epitope on the antigen. For the sake of simplicity, we will refer to this second antibody as a complementary antibody. The complementary antibody is immovably fixed on its test zone so that when liquid containing an antibody-antigen-label complex flows across a test zone that bears the complementary antibody specific to the antigen in the complex, the complementary antibody will attach to that antigen and fix the complex at that test zone. No labels are deposited at a test zone for which the specific antigen is not present. The test zones are readable by label-specific means. By that we mean, the human eye can read the test zones when a colored label is used; a radioisotope scanner or magnetic scanner can be used to read the test zones when radioisotopes or magnetic particles are used as the label, respectively.

After flowing past the series of test zones, the liquid flows across a control zone. The control zone contains a non-specific antibody such as goat anti-rabbit immunoglobulin G (IgG) or goat anti-mouse IgG that will bind with any labeled antibodies entrained in the liquid. Thus, the control zone will always have a positive stripe if the liquid sample has flowed the entire length of the test strip. A missing control zone stripe indicates that liquid carrying labeled antibodies did not flow across the control zone and, thus, may not have flowed across the test zones.

Using the technique of applying multiple test zones to an ICT test strip provides a rapid, economical, easy-to-use method of screening fecal samples for multiple enteric pathogens. In particular, the method can be used for rapid screening of the most common enteric pathogens that lead to outbreaks of diarrhea and/or for those enteric pathogens that require very specific treatment or have a particularly high mortality rate. Test kits that test according to the method of the present invention can be prepared for different geographical locations, taking into consideration the particularly relevant pathogens of the area. For example, test kits prepared for Australia or other parts of the world can include a test for *E. coli* O111, a pathogen that is rarely the cause of foodborne illness in the United States but is a significant cause in Australia.

Diarrhea may be caused by factors other than invasive enteric pathogens, and it is particularly useful for the treating physician to know whether, in the absence of various pathogens that are typically assayed, the diarrhea is associated with an inflammatory condition of the intestines or has other, non-inflammatory—and hence, generally, non-pathogenic—causes. Lactoferrin is an iron-binding bactericidal protein contained in granules in polymorphonuclear (PMN) leukocytes and is found in intestinal secretions, as well as in other secretions. Since the PMNs increase rapidly in number in response to an infection, the number of lactoferrin granules also increases. Studies have shown that the presence of fecal lactoferrin is a reliable general indicator of inflammation in the intestinal tract. See Choi et al.; To Culture or Not to Culture: Fecal Lactoferrin Screening for Inflammatory Bacterial Diarrhea, in: *Journal of Clinical Microbiology*, April 1996, p. 928–932. Because lactoferrin is also found in breast milk, fecal lactoferrin found in breast-fed infants is not an effective indicator of an inflammatory intestinal condition, as the presence of lactoferrin from breast milk will lead to false positives. Nevertheless, a method for detecting multiple enteric foodborne pathogens that includes a general indicator for an inflammatory condition of the intestines will provide the physician who is treating a patient other than a breast-fed infant with valuable information.

The assay for the presence of fecal lactoferrin according to the method of the present invention is similar to the assays for enteric pathogens—a first antibody that will bind specifically to the lactoferrin is conjugated to a label and a complementary antibody that will bind specifically to another epitope of the lactoferrin is immovably fixed on a lactoferrin test zone. If lactoferrin is present in the fecal sample, it will be labeled and fixed at the lactoferrin test zone and show up as a readable stripe across the test strip.

An assay that would indicate that the inflammatory enteric disease is caused by a bacterial, viral, or protozoan infection would provide further useful information to treating physicians. For example, if the test results for specific pathogens are negative and the test result for fecal lactoferrin is positive, the treating physician would like to know whether treatment with antibiotics is indicated. Antibiotics are effective against bacterial infections, but ineffective in combating viral infections. Furthermore, it may be detrimental to the health of the patient to prescribe antibiotics when not otherwise indicated and it is certainly not cost-effective to prescribe them as treatment for viral infection.

The assays for a bacteria marker, a virus marker, and a protozoa marker are similar to the assays described above for enteric pathogens and fecal lactoferrin. The assays for detecting markers may use a cocktail of antibodies or provide for multiple stripings of various antibodies. To detect a bacteria marker, for example, a cocktail containing various antibodies for common causes of infection may be applied to the bacteria marker test zone, or a series of test zones, each one marking a different bacteria, may be incorporated on an ICT test strip. Whether a cocktail of antibodies or multiple stripings is used, the immunochromatographic assay method remains the same: a first antibody that will bind to a particular first epitope on a bacteria is conjugated to a label and a complementary antibody that will bind specifically to a particular second epitope on the same bacteria is immovably fixed on a bacterial test zone. When a cocktail is used, the particular bacteria causing the infection will not be identified. A positive result for the bacteria marker will merely indicate that the patient is suffering from a bacterial infection caused by one of the bacteria to which antibodies were included in the cocktail. Similarly, assays for virus and protozoa markers can also be included on the test strip.

In the Preferred Embodiment, a two-panel device as disclosed by Chandler is used to test for the multiple pathogens, the lactoferrin, and the markers for bacteria and virus, although any ICT device that uses the sandwich technique for immunochromatographic assay is suitable for the method of the present invention.

DETAILED DESCRIPTION OF THE PREFERRED EMBODIMENT

The method of the present invention is directed at screening for inflammatory enteric disease by simultaneously determining the presence or absence of a multiplicity of inflammatory enteric disease indicators. In the Preferred Embodiment, the inflammatory enteric disease indicators are enteric pathogens, fecal lactoferrin, and markers for bacterial or viral infection, or the antigens derived from or consisting of the pathogens, the lactoferrin, and the bacteria and virus markers. The lactoferrin serves as a marker for an inflammatory condition of the intestines and the bacteria and virus markers serve as markers for a bacterial or viral infection, respectively, as the cause of the inflammatory condition. The two-panel ICT card disclosed by Chandler (U.S. Pat. No. 5,869,345), supra, is the device used in the Preferred Embodiment to perform the method of testing simultaneously for the indicators, although any number of suitable ICT devices known in the field of immunoassay may be used. In the Preferred Embodiment, the pathogens being assayed for are the diarrhea-causing pathogens *E. coli* O157, Campylobacter, Salmonella, Listeria, Shigella, and Yersinia, or a subcombination thereof. In an alternative embodiment, the enteric pathogens being assayed for may also include other enteric pathogens such as *E. coli* O26, *E. coli* O103, *E. coli* O111, *E. coli* O121, and *E. coli* O145. In the Preferred Embodiment, the extraction reagent added to the liquid in preparation for the test is a solution of 2.0% TWEEN 20, 0.05% sodium azide, and 0.5% sodium dodecyl sulfate in a 0.05M sodium citrate-sodium phosphate buffer of pH 6.5; two or three drops of this reagent are added to the sample.

Figure 1:
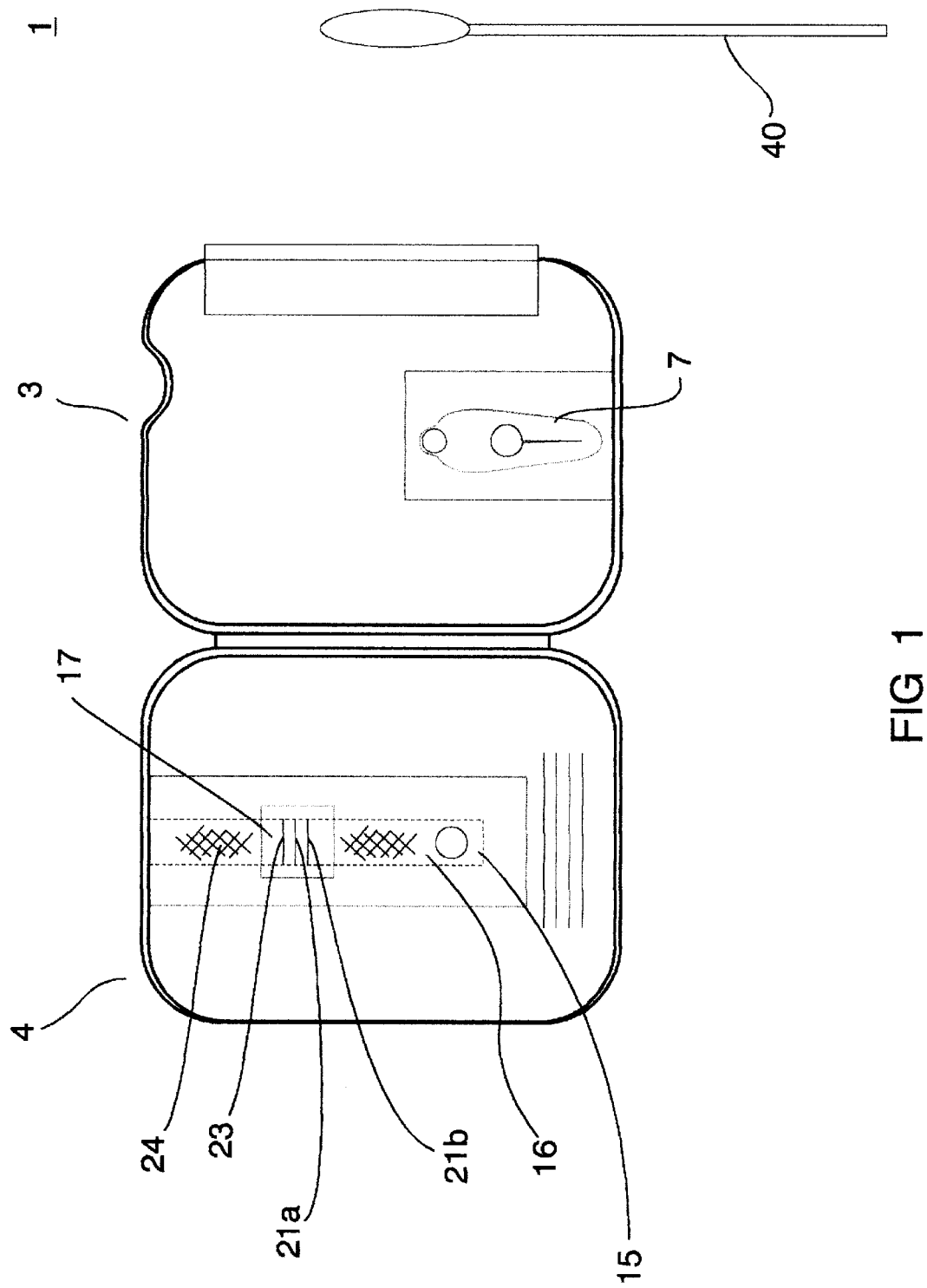
FIG. 1 is an illustration of the two-panel ICT device opened out flat, showing the swab well on the first panel and the test strip on the second panel.

The ICT test card 1 of the Preferred Embodiment, as shown in FIG. 1, contains a first panel 3 and a second panel 4. The first panel 3 contains a sample well 7; the second panel 4 contains a test strip 15. The test strip 15 is an assembly comprising a conjugate pad 16, a nitrocellulose pad 17, and an absorbent pad 24. Test strip 15 is shown in FIG. 1. The conjugate pad 16 has been impregnated with a conjugate of gold particles of 45 nm diameter and labeling binding partners, which, in the Preferred Embodiment, are affinity-purified polyclonal antibodies of anti- *E. coli* O157, Campylobacter, Salmonella, Listeria, Shigella, and Yersinia, or a subcombination thereof, and inflammatory enteric disease markers consisting of fecal lactoferrin, a non-specific bacteria antigen, and non-specific virus antigen. In the Preferred Embodiment, the gold is conjugated according to method described in "Preparation of Colloidal Gold Probes", Hughes, D. A. and Beesley, J. E. in: *Methods in Molecular Biology, Vol. 80: Immunochemical Protocols*, Second Edition, Pound, J. D., ed., Humans Press Inc., N.J, pp. 275–282, and in "Synthesis and Use of Colloidal Gold-Coupled Receptor Ligands" by Jennes et al. in: *Methods in Enzymology*, Vol. 124, Academic Press, 1986; the affinity purification is achieved as described by P. Tijssen in "Affinity Chromatography of Immunoglobulins or Antibodies" in: *Practice and Theory of Enzyme Immunoassays* by R. H. Burden and P. H. Van Knippedberg, eds., Elsevier, N.Y. 1985, pp. 105–114. In the Preferred Embodiment, the gold-conjugated antibodies are mixed with a drying agent and embedded into the conjugate pad 16. The drying agent used in the Preferred Embodiment is aqueous 5 mM sodium tetra borate, pH 8.0, containing 1.0% bovine serum albumin, 0.1% triton X-100, 2.0% TWEEN 20, 6.0% sucrose, and 0.02% sodium azide. The conjugate pad 16 releases the conjugated antibody-label complex when wetted by a liquid. Thus, when liquid from the prepared liquid sample is applied to the conjugate pad, the conjugated antibody-label complex is released from the pad and flows with the liquid. If antigen of any of the pathogens being assayed for is contained in the liquid, the conjugated antibody-label complex that can bind specifically with the particular antigen will bind to a particular first epitope on the antigen. The antigen is now labeled with the gold.

Downstream from the conjugate pad 16 is a nitrocellulose pad 17, as can be seen in FIG. 1. In the Preferred Embodiment the test assays for those antigens from fecal lactoferrin and the pathogens *E. coli* O157, *Campylobacter jejuni*, Salmonella, Listeria, Shigella and Yersinia, or a subcombination thereof, for bacteria antigens, and a virus antigens; fixed antibodies to the same antigens for which labeled antibodies have been conjugated on the conjugate pad 16 are used to prepare test zones 21a, 21b, . . . on the nitrocellulose pad 17, one test zone for each pathogen being assayed for, one test zone for the fecal lactoferrin, one test zone for a bacteria cocktail containing multiple bacteria antigens, and one for a virus cocktail containing multiple virus antigens. These fixed antibodies bind to the same antigens to which the labeled antibodies bind, but to a particular second epitope on the same antigen. A first test zone 21a is prepared on the nitrocellulose pad 17 by embedding fixed antibody to a first specific antigen being assayed for in the nitrocellulose pad 17. A second test zone 21b is prepared by embedding antibody of a second specific antigen, and so on, until distinct and separate test zones have been embedded in the nitrocellulose pad 17 for each pathogen and marker being assayed for. Shown in FIG. 1 are two test zones 21a and 21b, although as many test zones as pathogens and markers to be assayed will in actuality be embedded in the nitrocellulose pad 17 or in the carrier that is used to hold the immovably fixed antibodies. In the Preferred Embodiment, a solution comprising phosphate-buffered saline pH 7.4 with INTRA WHITE dye is used as a carrier fluid for the fixed antibodies. If the antibodies are polyclonal in nature, the antibodies are purified by the method of P. Tijssen mentioned above. A control band 23 is established by striping an antibody that binds non-specifically to the labeled antibodies, such as goat anti-rabbit IgG or goat anti-mouse IgG, on the surface of the nitrocellulose pad 17. This control antibody will bind with any of the labeled antibodies that are entrained by the liquid sample and carried to the control zone, thus ensuring that a control stripe will always be read at the control zone if the liquid has flowed the length of the strip.

Figure 2:
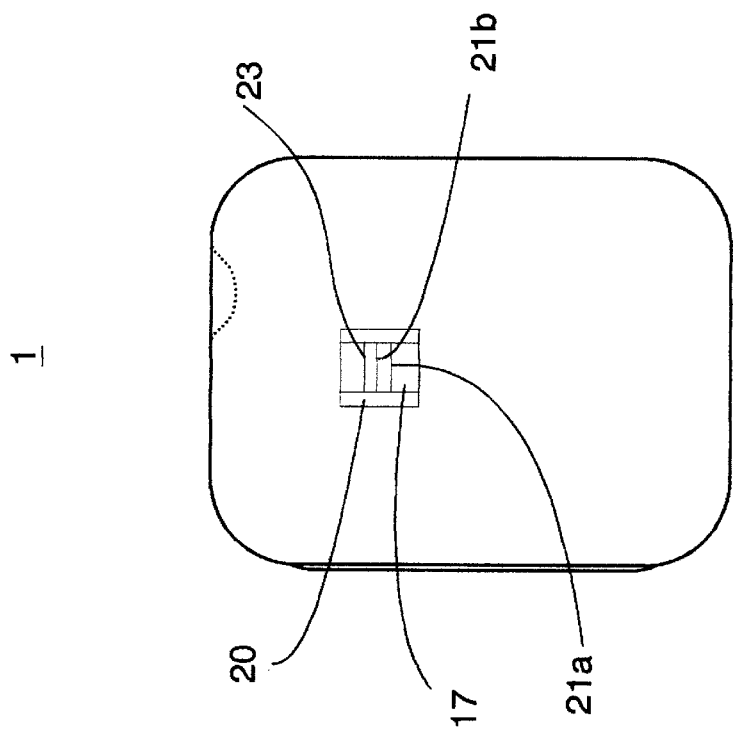
FIG. 2 is an illustration of the two-panel ICT device closed, showing the window exposing the test zones and control zone to view.

To screen for the presence of enteric pathogens, fecal lactoferrin, bacteria markers and virus markers according to the method of the present invention, an extraction reagent is added to a fecal sample and the fecal sample is applied to an ICT test device. In the Preferred Embodiment, a fecal sample is collected on a swab 40 and the swab 40 is inserted into the swab well 7, shown in FIG. 1. Two or three drops of the extraction reagent are added to the swab well 7 and the device is closed. Within a few minutes, depending on the particular assay being performed, one can view the test results through a window 20 on the device, as shown in FIG. 2. One or more visible bands or stripes 21a, 21b, . . . are positive indicators for the presence of a specific pathogen being assayed and/or of lactoferrin, the bacteria marker, and the virus marker. If a control stripe 23 is absent, the test is invalid.

While a Preferred Embodiment is disclosed herein, this is not intended to be limiting. Rather, the general principles set forth herein are considered to be merely illustrative of the scope of the present invention and it is to be further understood that numerous changes may be made without straying from the scope of the present invention.

We claim:

1. A method for testing a fecal liquid sample obtained from a patient suffering from diarrhea, other than a breast-fed infant, in an effort to identify the causative organism for the diarrhea and thereby enable the timely prescription of a medicament known to be effective against said causative organism or the diagnosis that the condition has no causative organism, which method comprises
   (1) contacting said sample essentially simultaneously with tagged antibodies to each of (a) fecal lactoferrin and (b) at least two organisms known to be causative of diarrhea in humans selected from among the group consisting of bacteria, viruses and protozoa;
   (2) contacting said sample and said tagged antibodies with a solid surface to which is immovably bound (a) a stripe of complementary antibodies to fecal lactoferrin and (b) stripes separate from the fecal lactoferrin complementary antibody stripe and from each other, of complementary antibodies to each of the organisms selected to be tested for in step (1) (b)
   (3) allowing sufficient incubation time to permit the formation of "sandwiches" of tagged antibody and fixed antibody interlayered with any antigenic binding partner to each of the antibodies that was present in the sample;
   (4) inspecting the immovably fixed antibody stripes on the solid surface to detect which lines, if any exhibit color, radioactivity or magnetization imparted by the tag of the tagged antibody and indicative of the presence of fecal lactoferrin and/or of at least one of said organisms; and
   (5) from the observed result determining; (a) that the patient should be treated for infection by the particular organism, the antibodies to which formed a tagged "sandwich" stripe, or (b) if none of the separate stripes of antibodies to said organisms formed a tagged "sandwich" stripe but the fecal lactoferrin stripe did so, that further timely effort should be promptly made to locate the bacteria responsible for the patient's diarrhea, or (c) if neither the fecal lactoferrin antibody stripe nor the separate stripes of antibodies to organisms known to be causative of diarrhea formed a tagged "sandwich" stripe, that the patient should be advised the diarrhea condition is not caused by bacteria or by any of the viral or protozoan organisms, antibodies for which were included in the test.

2. A method according to claim 1 in which the sample is contacted in step (1) with tagged antibodies to fecal lactoferrin and with tagged antibodies to each of at least two separate bacteria known to cause diarrhea in humans and the mixture of sample and tagged antibodies is then contacted with a solid surface to which is immovably bound (a) a separate stripe of complementary antibodies to fecal lactoferrin and (b) separate stripes of complementary antibodies to each of the separate bacteria being tested.

3. A method according to claim 1 in which the sample is contacted in step (1) with tagged antibodies to fecal lactoferrin and tagged antibodies to each of a group of organisms causative of diarrhea that are known to be indigenous to the geographic region of the world in which the patient's condition is believed to have originated.

4. A method according to claim 2 in which the immovably bound stripe of antibodies to fecal lactoferrin forms a tagged antibody-antigen fixed antibody "sandwich" line in step (3), but none of the at least two lines of antibodies to specific bacteria forms such a tagged sandwich stripe and accordingly, step (5) is followed by mixing sample from the same patient with tagged antibodies to at least two bacteria known to be causative of diarrhea in humans but not tested for in the initial test, followed by incubating this mixture with a solid surface upon which has been placed an immovably fixed separate stripe of complementary antibodies to each of the bacteria represented by tagged antibodies in the sample/tagged antibody mixture, inspecting the line or lines upon which a tagged "sandwich" has formed and determining from what is thus observed the cause of the patient's diarrhea and the treatment to be given the patient.

5. A process according to claim 1 in which the sample is applied to an immunochromatographic ("ICT") strip upon which tagged antibodies to fecal lactoferrin and to the selected pathogenic organisms have been movably deposited and the sample and the various tagged antibodies are allowed to flow together to a region of the ICT strip upon which separate stripes of immovably fixed antibodies to fecal lactoferrin and to each of the selected organisms has been immovably fixed.

6. A process according to claim 2 wherein the bacteria are selected from among *Campylobacter jejuni*, Salmonella, Listeria, Shigella Yersinia, Cryptosporidium Giardia and at least one strain of *E. coli*.

7. A process according to claim 6 wherein *E. coli* strain O157 is one of the selected bacteria.

* * * * *